United States Patent [19]

Kiefer

[11] Patent Number: 5,594,176

[45] Date of Patent: Jan. 14, 1997

[54] SCAN ASSEMBLY AND METHOD FOR TRANSFERRING POWER AND DATA ACROSS A ROTARY INTERFACE

[75] Inventor: Karl F. Kiefer, Woodlands, Tex.

[73] Assignee: Gas Research Institute, Chicago, Ill.

[21] Appl. No.: 497,775

[22] Filed: Jul. 3, 1995

Related U.S. Application Data

[63] Continuation-in-part of Ser. No. 222,621, Apr. 5, 1994.

[51] Int. Cl.⁶ ............................................. G01R 33/12
[52] U.S. Cl. ........................... 73/623; 324/238; 324/240; 324/242; 367/25; 367/69; 367/86
[58] Field of Search ................... 73/623, 622, 635, 73/637, 638, 639, 640, 618; 324/238, 240, 242; 367/86, 25, 27, 28, 69

[56] References Cited

U.S. PATENT DOCUMENTS

| | | | |
|---|---|---|---|
| 2,723,357 | 11/1955 | Valkenburg et al. | 310/8.7 |
| 3,714,816 | 2/1973 | Miller | 73/71.5 |
| 3,763,694 | 10/1973 | Rathburn et al. | 73/71.5 |
| 4,055,990 | 11/1977 | Topping | 73/623 |
| 4,131,018 | 12/1978 | Muller et al. | 73/432 |
| 4,170,755 | 10/1979 | Mansson | 324/238 |
| 4,285,243 | 8/1981 | Collingwood | 73/623 |
| 4,289,025 | 9/1981 | Norel et al. | 73/152 |
| 4,302,976 | 12/1981 | Bull | 73/639 |
| 4,304,134 | 12/1981 | Rouse et al. | 73/634 |
| 4,506,549 | 3/1985 | Thome | 73/582 |
| 4,615,218 | 10/1986 | Pagano | 73/639 |
| 4,621,532 | 11/1986 | Takagi et al. | 73/623 |
| 4,691,572 | 9/1987 | van den Berg et al. | 73/643 |
| 4,718,277 | 1/1988 | Glascock | 73/622 |
| 4,735,087 | 4/1988 | Homrani et al. | 73/597 |
| 4,769,598 | 9/1988 | Krieg et al. | 324/219 |
| 4,829,486 | 5/1989 | Broding | 367/25 |
| 4,837,753 | 6/1989 | Morris et al. | 367/69 |
| 5,007,291 | 4/1991 | Walters et al. | 73/640 |
| 5,014,711 | 5/1991 | Nagasaki | 128/660.07 |
| 5,046,033 | 9/1991 | Andreasen et al. | 364/580 |
| 5,170,346 | 12/1992 | Crawford et al. | 364/413.16 |
| 5,204,622 | 4/1993 | McCaslin et al. | 324/220 |
| 5,254,944 | 10/1993 | Holmes et al. | 324/220 |

*Primary Examiner*—Hezron E. Williams
*Assistant Examiner*—Rose M. Finley
*Attorney, Agent, or Firm*—Hopkins & Thomas

[57] ABSTRACT

An ultrasonic scan assembly for use in inspecting downhole gas pipes comprises a sensor section which rotates in relation to an end section that remains essentially level forming a rotating interface. The sensor section includes at least one ultrasonic transducer for transmitting interrogating pulses into a pipe wall and for receiving return pulses that are analyzed for determining the maintenance and repair needs of the gas pipe. Provided in the scan assembly is a rotary transformer for magnetically coupling signals, such as return pulse data or power, across the rotating interface of the scan assembly. The rotary transformer includes a primary winding on one section of the scan assembly and a secondary winding on another section of the scan assembly. The primary windings and secondary windings associated with respective sections of the scan assembly can be placed in parallel or concentric relationship.

8 Claims, 11 Drawing Sheets

SCAN ASSEMBLY AND METHOD FOR TRANSFERRING POWER AND DATA ACROSS A ROTARY INTERFACE

The present patent application is a continuation-in-part application of a co-pending patent application entitled "Scan Assembly Structure", filed on Apr. 5, 1994, assigned Ser. No. 08/222,621. The foregoing application is incorporated herein by reference.

FIELD OF THE INVENTION

The present invention relates generally to the inspection of buried natural gas pipes and more particularly, to a scan assembly and method for inspection gas pipes for transferring power and/or data across a rotary interface from a rotational sensor section to a stationary end section.

BACKGROUND OF THE INVENTION

Thousands of miles of buried natural gas pipes of varying size and formed from various materials are presently in service. All of these pipes are in some state of progressive degradation. In most instances, the extent of such degradation is unknown, and hence, the serviceability of the pipes is similarly unknown. This lack of information with the respect to the degree of degradation results in unforeseen gas pipe leaks and/or breaks, and necessitates the expending of substantial time and expense in locating these defects so that repairs and/or replacement can be made. Because of the need to detect conditions which might result in gas pipe breaks and/or leaks, an apparatus has been developed for inspecting gas pipes, and such apparatus is referred to as a pipe line "pig" or "mouse." For purposes of clarity, such apparatus are hereafter generally referred to as scan assemblies. Such pipe line scan assemblies typically include a housing with a plurality of sensors mounted to the outer surface thereof in a predetermined configuration or array to contact the inner surface of the gas pipe. Since the sensors are in a predetermined configuration or array, complete inspection of the wall of the gas pipe is generally not possible, i.e., the portion of the pipe wall between two adjacent sensors is typically not inspected. Thus, complete inspection of the wall would require an inordinate number of sensors.

In an attempt to achieve close to complete inspection, one scan assembly has incorporated rotational movement of its sensors so that, as the scan assembly advance axially down the pipe, a helical scan pattern is produced. This is accomplished by providing the scan assembly with a central, rotatable sensor section interposed two end sections which remain stationary relative to the rotating sensor section. Mounted to the sensor section are one or more sensors, such as ultrasonic transducers.

Since the aforementioned scan assembly incorporates a rotating sensor section, there must be provided means for transferring power and data across the rotating interface between the sensor section and the stationary end section(s). Two methods available for accomplishing the transfer of power and data are (1) the use of slip rings and (2) the use of low level radio frequency (RF) data transmission. Unfortunately, both of these methodologies have several disadvantages, some of which are described below. For example, slip rings introduce noise into the transmitted signal as a function of the coefficient of friction vibration. To reduce the effect of the added noise, the transmitted signals are generally passed as logic level signals, and preferably, a digitized rather than analog signal. Thus, a signal at the sensor section must be processed before being transmitted to the stationary section. This requires miniaturized electronic circuitry be mounted in the sensor section for processing of the signal so that it can be transmitted to the stationary section. The mechanical drag produced by the contact of the slip rings increases the energy lost in the motor utilized to rotate the sensor section. Further, slip rings are physically complex, and therefore, present service concerns in regard to breakage and maintenance. An RF transmitter/receiver configuration does not have the service concerns of slip rings but requires the sensor section to include more conditioning circuitry in order to multiplex the signal if more than one is to be transmitted, and to modulate the multiplexed signals onto a high frequency carrier. This is more costly and consumes more power than slip ring, not to mention that power cannot be transmitted in this manner.

In addition to scan assemblies that utilize ultrasonic transducers as sensors, scan assemblies can also be equipped with other diagnostic tools such as video cameras, temperature sensors, or humidity sensors. In operation, several scan assemblies having different diagnostic tools thereon are often linked together to form an inspection train whereby power and data is passed from scan assembly to scan assembly and to above ground or "uphole" electronics units via an umbilical cord attached to the first scan assembly in the train.

In view of the foregoing, it has become desirable to develop a method and apparatus that provides an efficient, dependable and economical means for transmitting power and/or data from the rotational sensor section to the stationary section of a scan assembly.

SUMMARY OF THE INVENTION

An object of the present invention is to overcome the deficiencies and inadequacies in the prior art as described above and as generally known in the industry.

Another object of the present invention is to enable a more accurate and noise free transfer of data in a scan assembly between rotating and stationary sections.

Another object of the present invention is to improve the ability and efficiency of an ultrasonic downhole scan assembly in transferring data and power within a single scan assembly and along an inspection train of multiple scan assemblies with a minimum amount of support electronics.

Another object of the present invention is to improve the signal-to-noise ratio of a downhole ultrasonic scan assembly.

Briefly stated, the present invention is a scan assembly for use in the inspection of downhole gas pipes which comprises a sensor section which rotates in relation to an end section that remains essentially stationary. The sensor section includes at least one ultrasonic transducer for transmitting interrogating pulses into the pipe wall and for receiving return pulses from a tangent. The received return pulses are transmitted from the end section of the scan assembly to above ground electronics via an umbilical cord. In order to transmit signals, such as return pulse data or power, across the rotating interface between the rotating sensor section and the stationary end section of the scan assembly, a rotary transformer is provided which magnetically couples the winding circuit of the rotating sensor section and the winding circuit of the stationary end section. Note, that transmission in either direction across the rotary transformer is possible. The rotary transformer comprises a plurality of winding pairs, each pair dedicated to the transmission of a particular signal, or a single winding pair in which case the multiple signals are multiplexed together and then modulated onto a high frequency carrier for transmission across the rotating interface of the scan assembly.

The present invention can also be thought of as a method for transferring power and/or return pulse data signals across a rotating interface of a scan assembly that is used to inspect gas pipes, wherein the scan assembly comprises a rotating sensor section having a first electrical circuit and a stationary end section having a second electrical circuit wherein the method comprises the following steps. One step is to place the signal to be transmitted on either the first electrical circuit of the rotating sensor section or the second electrical circuit of the stationary end section. Another step is to magnetically couple the first electrical circuit and the second electrical circuit, whereby the signal on the electrical circuit is transferred onto the other electrical circuit.

In addition to achieving all of the aforementioned objects, the present invention has numerous other advantages, a few of which are delineated hereafter as examples.

An advantage of a rotary transformer in accordance with the present invention is that it requires no support electronics to amplify or digitize the signal transmitted across the transformer.

Another advantage of a rotary transformer in accordance with the present invention is that it consumes essentially no power.

Another advantage of a rotary transformer is that there is no mechanical drag because the windings do not touch, and thus, the amount of energy lost in the motor rotating the sensor section is reduced.

Another advantage a rotary transformer in accordance with the present invention is that it is relatively inexpensive, takes up little space, and provides a virtually noise-free transmission.

Other objects, features, and advantages of the present invention will become apparent from the following description when considered in conjunction with the accompanying drawings. All such additional objects, features, and advantages of the present invention are intended to be included herein.

BRIEF DESCRIPTION OF THE DRAWINGS

The present invention, as defined in the claims, can be better understood with reference to the following drawings. The drawings are not necessarily to scale, emphasis instead being placed upon clearly illustrating the principles of the invention. Moreover, like reference numerals designate corresponding parts throughout the several views.

DETAILED DESCRIPTION OF THE PREFERRED EMBODIMENT

Figure 1:
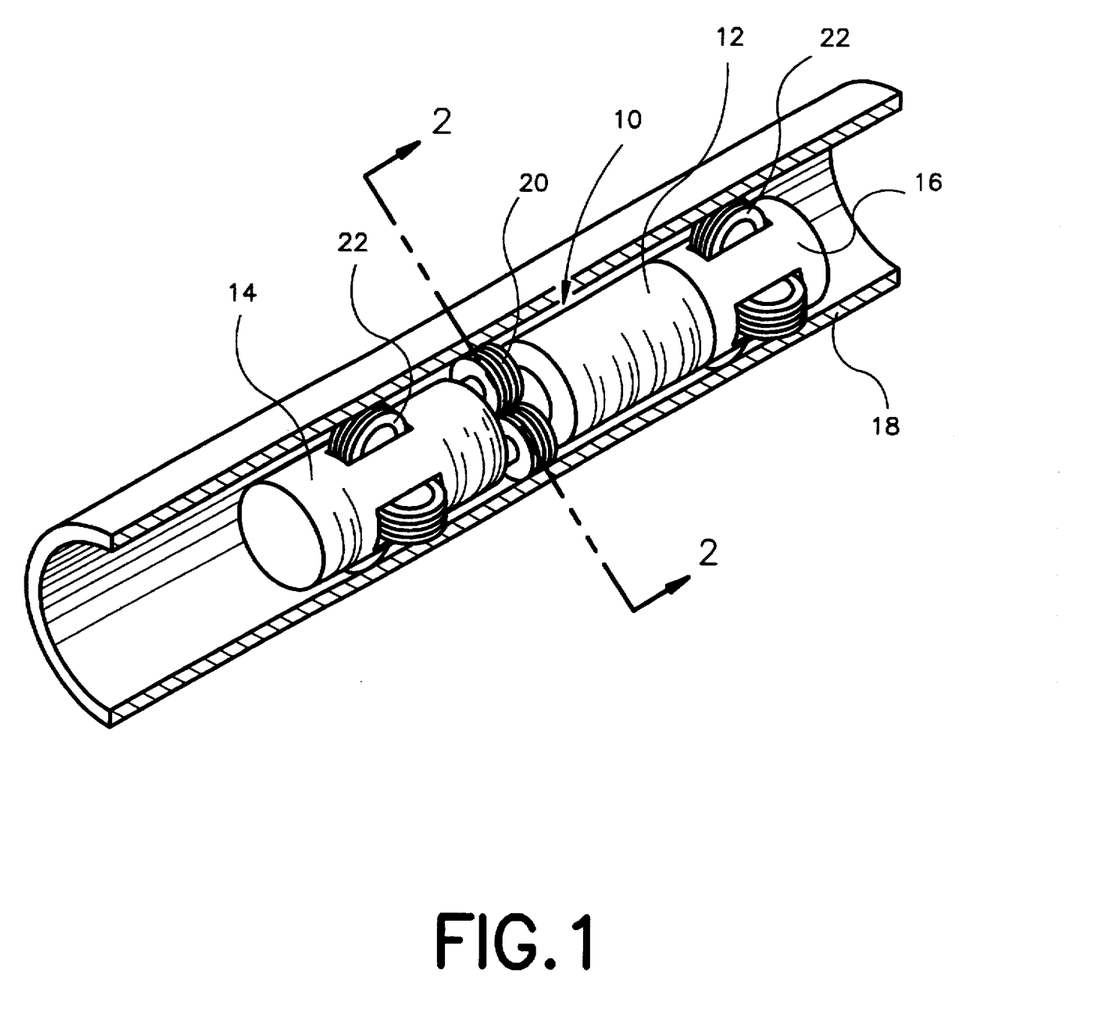
FIG. 1 is a perspective view, partially cut-away in cross-section, of a first embodiment of the scan assembly for use with the present invention.

Referring now to the drawings where the illustrations are for the purpose of describing the preferred embodiment of the present invention and are not intended to limit the invention described herein, FIG. 1 is a perspective view of a scan assembly 10 which can be utilized to transmit ultrasonic interrogating pulses into an object whose material is to be inspected and to receive return pulses from imperfections, flaws or occlusions within the material or from surfaces thereon. The scan assembly 10 includes a sensor section 12 interposed between a front section 14 at one end of the assembly 10 and a rear section 16 at the other end thereof. The scan assembly 10 is receivable within the object to be inspected, such as a gas pipe 18, and is moveable along the longitudinal axis of the gas pipe 18. The sensor section 12 includes a pair of scan rollers 20 which are angularly positioned approximately 180 degrees relative to one another and canted slightly in the direction of travel of the scan assembly 10 through the gas pipe 18 so as to drive the scan assembly 10 therethrough. The canting or offsetting of the scan rollers 20 causes the scan assembly 10 to pull itself through the gas pipe 18 as the scan rollers 20 rotate. The front section 14 and the rear section 16 of the scan assembly 10 are provided with wheels 22 which are angularly positioned approximately 90 degrees relative to one another in each section 14, 16, and are oriented along the longitudinal axis of the assembly 10. The wheels 22 are coupled to rotation position sensors (not shown) so that the movement of the scan assembly 10 within the gas pipe 18 and the location of the scan assembly 10 therein can be accurately monitored. A biasing mechanism (not shown; e.g., a spring) are provided and apply a radially outwardly directed force to each of the wheels 22 permitting the scan assembly 10 to be used within gas pipe 18 of various inner diameters.

Figure 2:
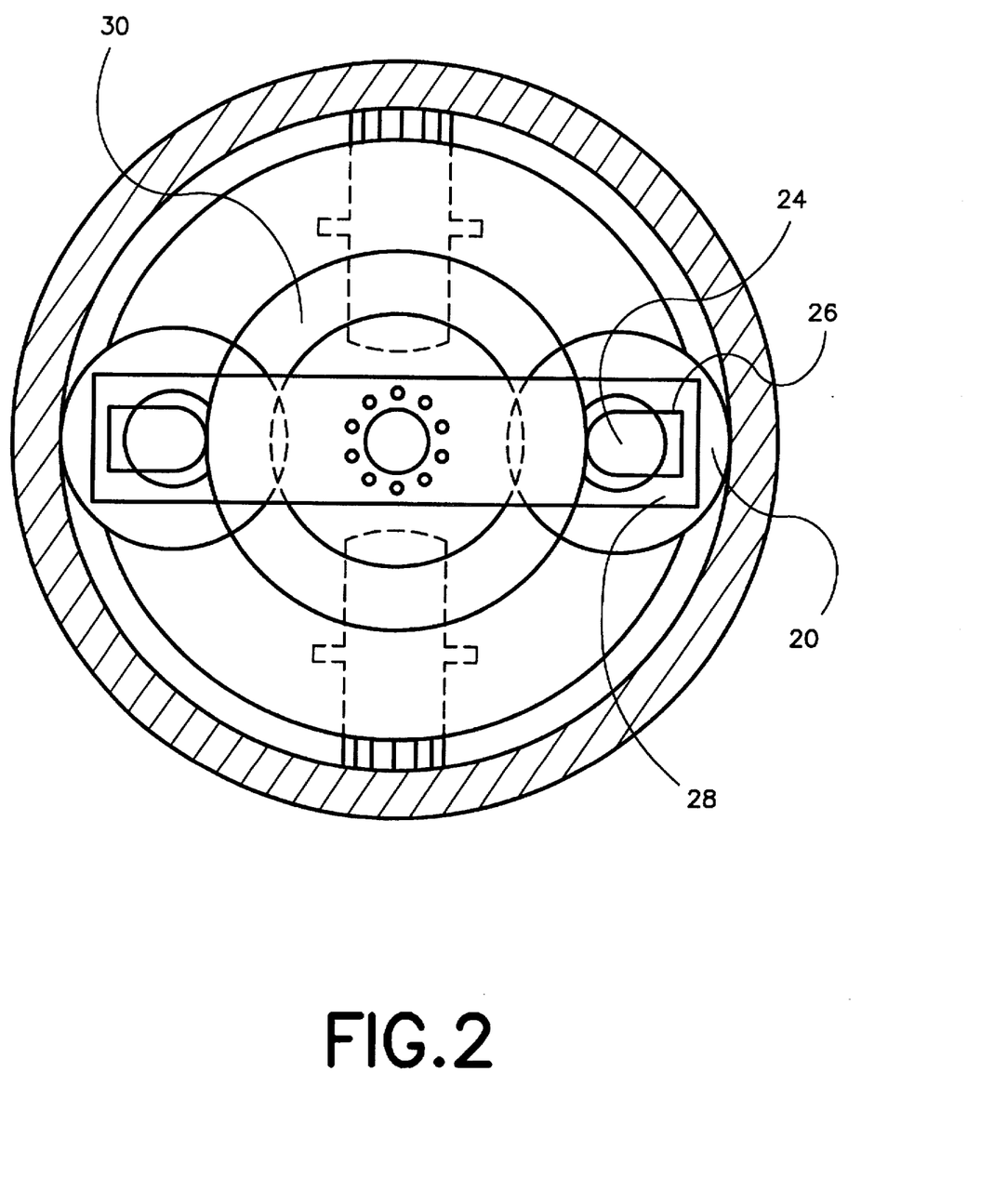
FIG. 2 is a partial cross-sectional view of the scan assembly of FIG. 1 taken substantially along lines 2—2 in FIG. 1.

Referring now to FIG. 2, an axle 24 about which a scan roller 20 rotates is received within an elongated slot 26 provided in either end of a crank arm 28 which is rotated by a scan motor 30 located within front section 14 of scan assembly 10. The elongated slot 26 permits radial movement of the scan roller 20 therein. A biasing mechanism (not shown; e.g., a spring) are provided and apply a radially outwardly directed force to the axle 24 and the scan roller 20 causing the scan roller 20 to grippingly engage the surface defining the inner diameter of the wall of the gas pipe 18. Rotation of the crank arm 28 by the scan motor 30 causes the scan roller 20 at either end thereof to similarly rotate resulting in the scan assembly 10 being propelled by the scan rollers 20 through the gas pipe 18.

Figure 3:
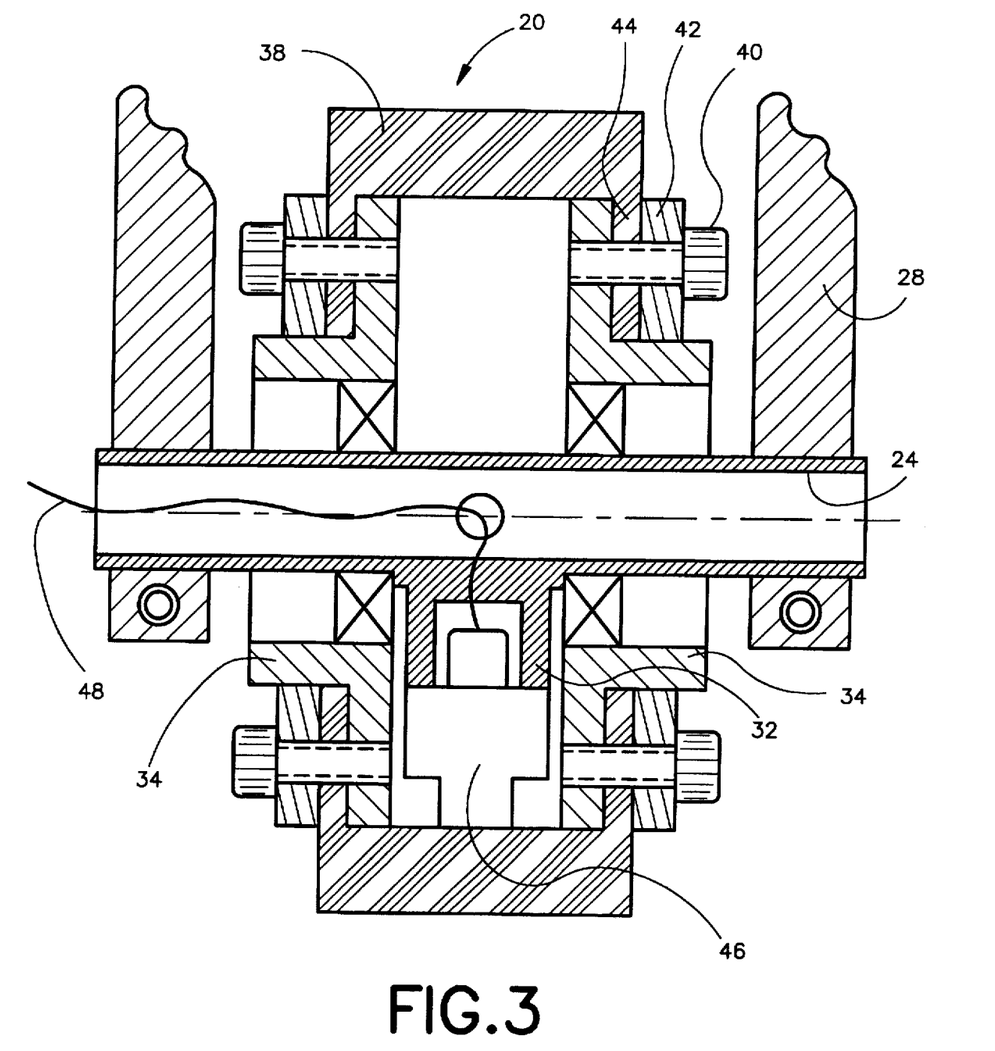
FIG. 3 is a cross-sectional view of the scan roller of the scan assembly of FIG. 1.

Referring now to FIG. 3, a cross-sectional view of a scan roller 20 rotationally mounted to the axle 24 is illustrated. The scan roller 20 includes a hub 32 through which an axle 24 is received and attached thereto. The hub 32 is interposed with a pair of spaced-apart side plates 34. The side plates 34 are rotationally mounted to the axle 24 and the hub 32 by a pair of sealed bearings 36. A polymer tire 38 is attached to the side plates 34 by fasteners 40 which are received through both a backing plate 42 and an inwardly directed lip of the tire 38 which threadingly engages the side plate 34. An ultrasonic transducer 46 is received within the scan roller 20 and attached to the hub 32 therein. An electrical conductor 48 is connected to the ultrasonic transducer 46 and passes through the axle 24 permitting actuation of the transducer 46 resulting in the production of ultrasonic interrogating pulses which are transmitted through the wall of the tire 38 into the wall of the gas pipe 18. When the interrogating pulses encounter an interface, return pulses are directed back to and received by the transducer 46 through the wall of tire 38. Such interfaces include, but are not limited to, the surface defining the inner diameter of the wall of the gas pipe, the surface defining the outer of the wall of the gas pipe, and any imperfections and/or flaws within the walls of the gas pipe.

Figure 4:
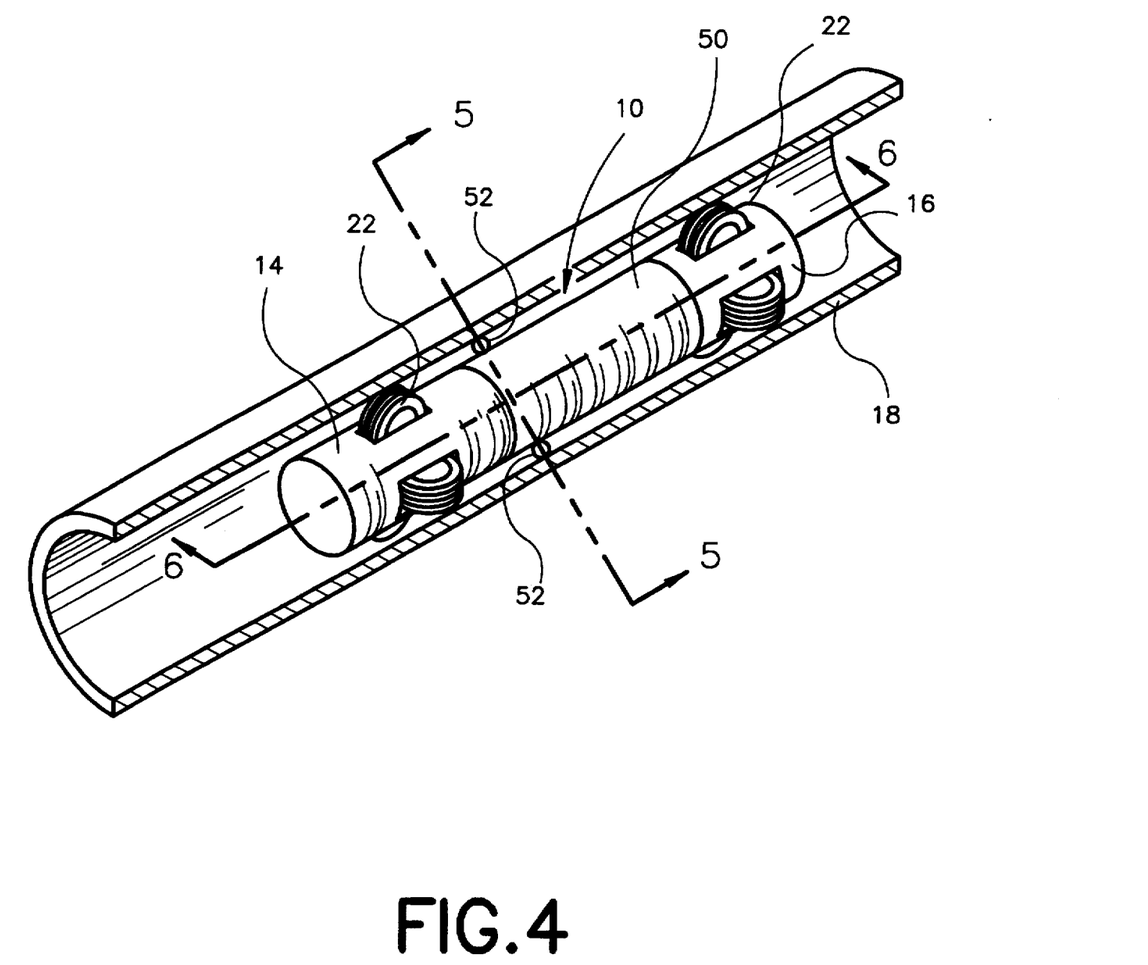
FIG. 4 is a perspective view, partially cut-away in cross-section, of an alternative embodiment of a scan assembly for use with the present invention.
Figure 5:
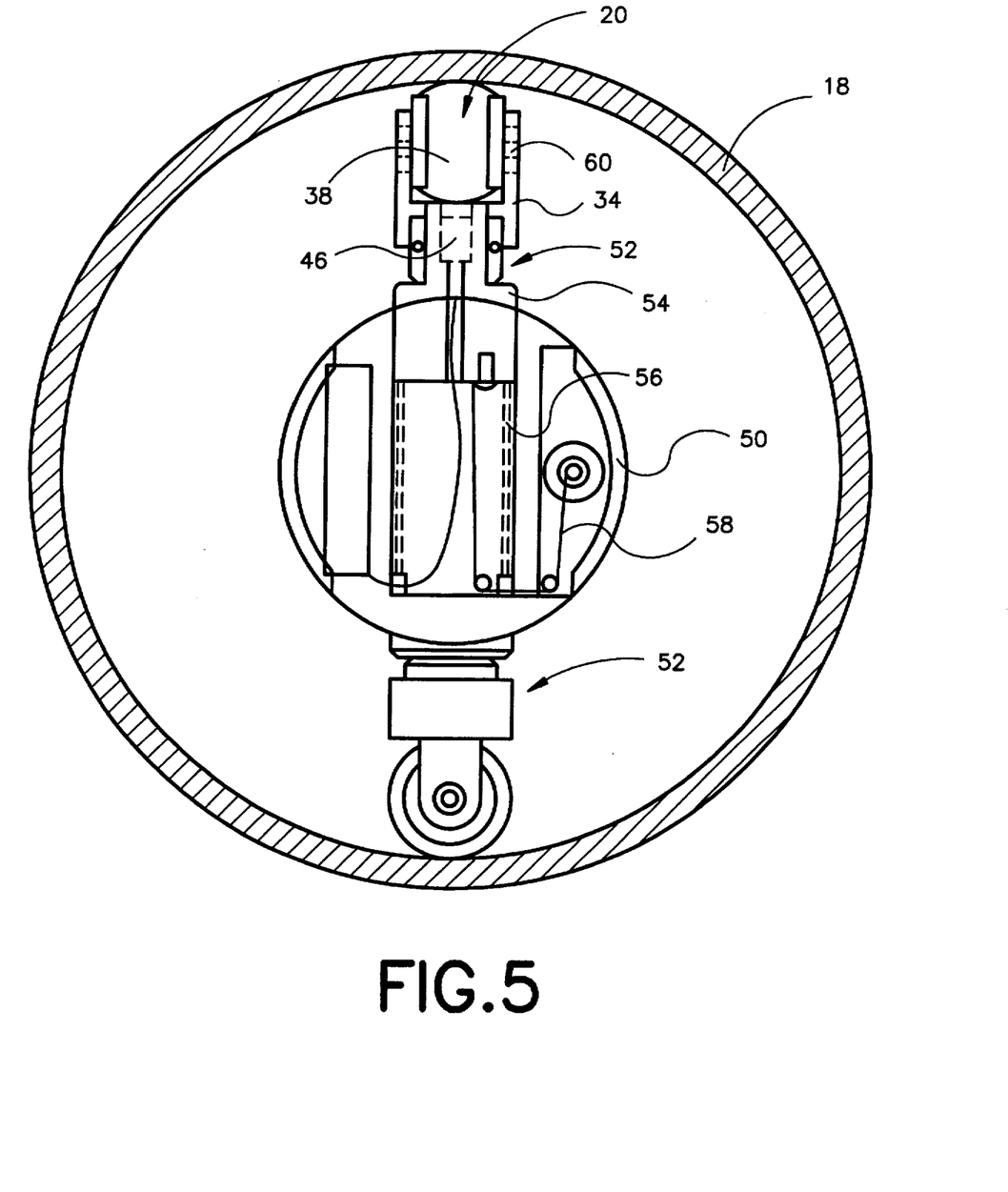
FIG. 5 is a partial cross-sectional view of the scan assembly of FIG. 4 taken substantially along lines 5—5 in FIG. 4.

A perspective view of another type of scan assembly 10 is shown in FIG. 4. In this instance, the scan assembly 10 is not self-propelling but requires the application of an externally applied force thereto by a mechanism such as a push rod to propel same though the gas pipe 18. In this case, the scan assembly 10 includes a sensor section 50 interposed between the front section 14 and the rear section 16 of the scan assembly 10 and rotatable about the longitudinal axis of the scan assembly 10. Referring now to FIG. 5, each scan roller 20 is part of a scan roller assembly 52, and two scan roller assemblies 52 are received within the sensor section 50 and are angularly positioned 180 degrees relative to one another. Each scan roller assembly 52 is comprised of a telescoping scanning arm 54, a scan roller 20 rotatably connected to one end of the scanning arm 54, an extension spring 56 contacting the other end of the scanning arm 54 and biasing arm 54 radially outwardly from the sensor section 50, and a retraction cable 58 which assists in withdrawing the scanning arm 54 into the sensor section 50. Each retraction cable 58 is connected to a linear variable distance transducer (not shown) which provides information as to the radius of the inner diameter of the gas pipe 18 as a function of the angular orientation of the scan roller assembly 52. Such information can be utilized to provide data as to the shape and ovality of the inner diameter of the gas pipe.

When the scan roller assemblies 52 are radially extended relative to the sensor section 50, their associated tires 38 grippingly and pliantly engage the surface defining the inner diameter of the wall of the gas pipe. Conversely, when the scan roller assemblies 52 are in the fully retraced condition, their associated tires 38 are within the sensor section 50. In either case, the tires 38 are formed from a low bulk modulus polymer material to provide an optimum mechanical impedance for the passage of ultrasonic pulses therethrough. It should be noted that the ultrasonic transducer 46 might be mounted externally of the scan roller 20, as shown by the phantom lines in FIG. 5. When the transducer 46 is so mounted, the scan roller 20 will be provided without an axle 24, and will be supported for rotation by outwardly directed journals 60 (shown in phantom lines) attached to the side plates 34.

Figure 6:
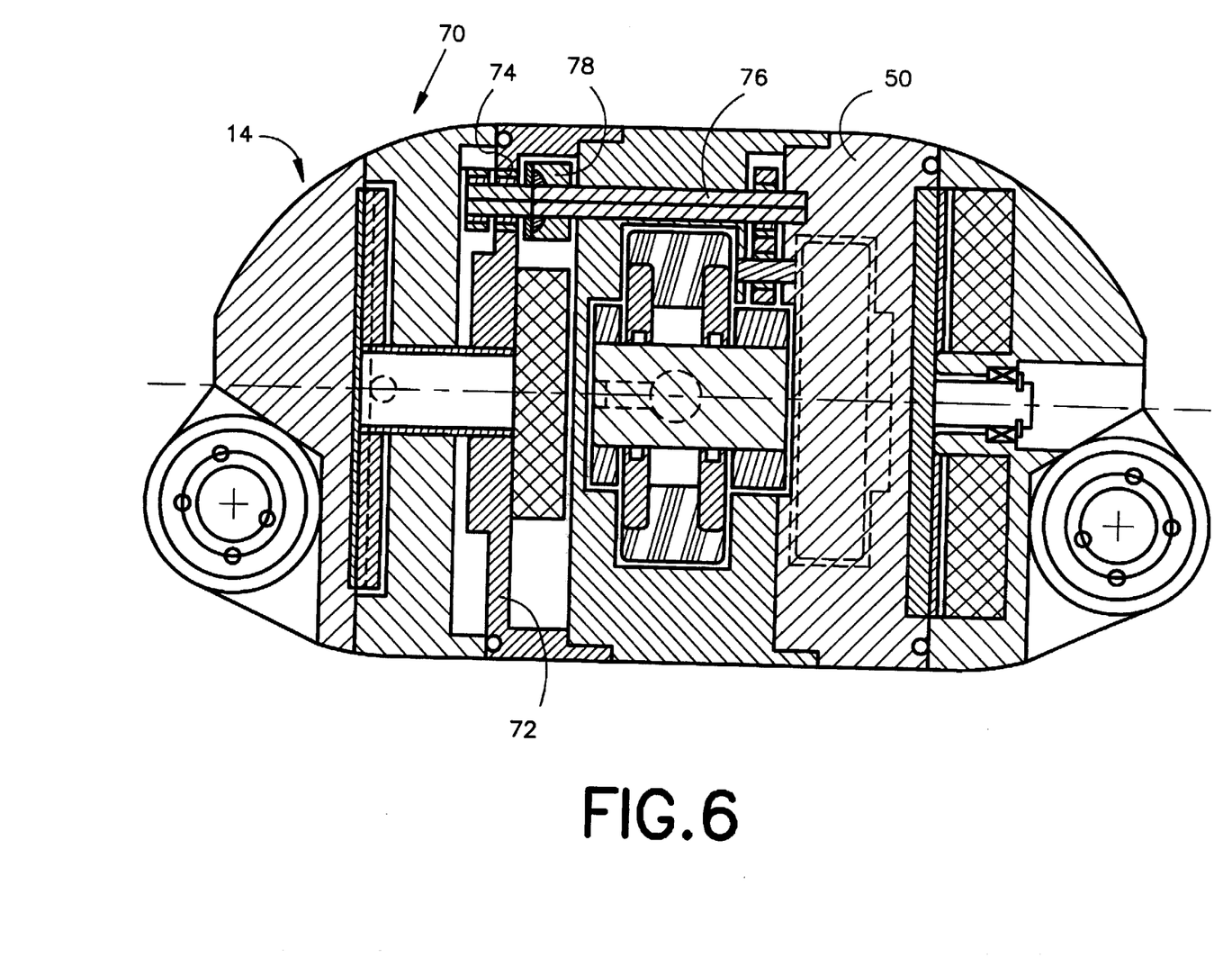
FIG. 6 is a partial cross-sectional view of the scan assembly of FIG. 4 taken substantially along lines 6—6 in FIG. 4, showing the drive for the sensor section within same.

Referring now to FIG. 6, the drive for the sensor section 50 is illustrated. The drive is comprised of a reversible electric motor 70 located in front section 14 of the scan assembly 10. The output shaft of motor 70 is keyed to the sensor section 50 causing rotation thereof. A ring gear 72 is similarly keyed to the output shaft of the motor 70 and engaged an idler gear 74 which is connected to a shaft 76 within the sensor section 50 via a ball sprague clutch assembly 78. The shaft 76 is, in turn, connected to two retraction cables 58, each connected to a scanning arm 54. During clockwise rotation of the output shaft of motor 70, the ball sprague clutch assembly 78 is disengaged and the sensor section 50 is rotated by a motor 70 and each scanning arm 54 moves radially outwardly under the urging of spring 56 causing its associated tire 38 to contact the surface defining the inner diameter of the wall of the gas pipe. If an obstruction in the gas pipe is encountered, the motor 70 is stopped and reversed causing its output shaft to rotate counter-clockwise. In this situation, the ball sprague clutch assembly 78 becomes engaged and the motor 70 "reels-in" the cables 58 causing the scanning arms 54 to retract radially inwardly into the sensor section 50. It should be noted that the wheels 22 on the front section 14 and the rear section 16 of the scan assembly 10 prevent rotation of these sections with respect to the sensor section 50 as the scan assembly 10 moves through the gas pipe 18.

Regardless of whether the scan assembly 10 is in the form of that illustrated in FIG. 1 or FIG. 4, provision must be made for the transmission of the return pulses or other data from the rotating sensor section 12, 50 to the rear section 16 of the scan assembly 10. Once the foregoing return pulses have been transmitted to the rear section 16 of the scan assembly 10, they can be transmitted to an "uphole" electronics unit (not shown) by an umbilical cord (not shown). Moreover, if several scan assemblies are configured in an inspection train, data collected by a downstream scan assembly must be transmitted back through each scan assembly 10 of the train to the first scan assembly which is connected to the umbilical cord for transmission of the data to the "uphole" electronics unit. In addition, power to operate each of the scan assemblies and control information must also be transmitted from scan assembly to scan assembly in a reverse manner from the first scan assembly to the downstream scan assemblies.

In order to transmit a return pulses from the sensor section 12, 50 to the rear section 16 of the scan assembly 10, it has been determined that a noncontacting, rotary transformer is preferable for various reason. For instance, a rotary transformer requires no support electronics to amplify or digitize a signal transferred across the transformer and consumes essentially no power. In addition, a rotary transformer is relatively inexpensive, takes up little space and provides a virtually noise-free transmission.

Figure 7:
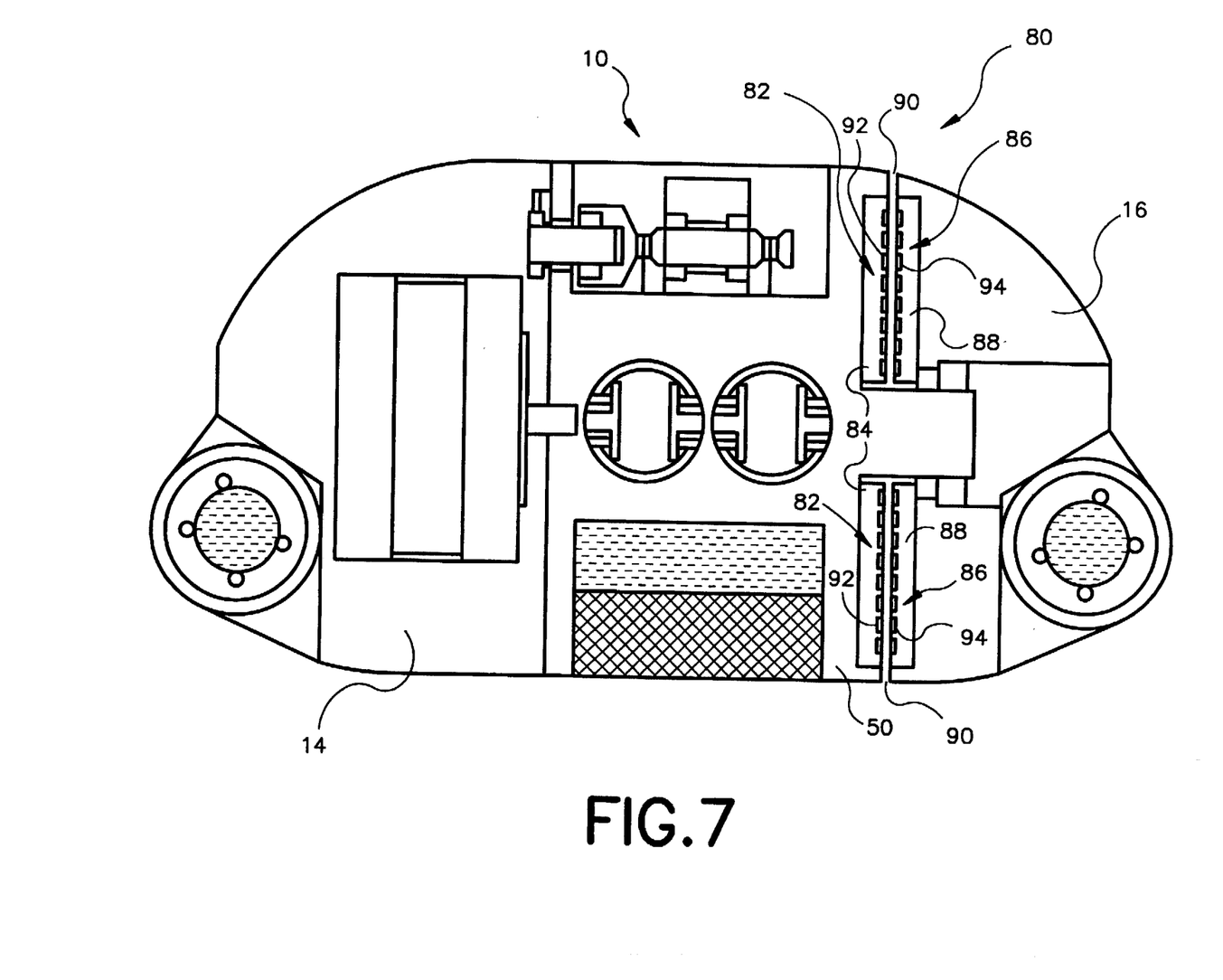
FIG. 7 is a cross-sectional view of a scan assembly showing a first embodiment of a rotary transformer in accordance with the present invention.

A first embodiment of a rotary transformer in accordance with the present invention is rotary transformer 80 shown in FIG. 7 within the scan assembly 10 of FIG. 4, though it can be appreciated that transformer 80 can just as easily be incorporated within the scan assembly 10 of FIG. 1. In the presented configuration, the rotary transformer 80 is comprised of primary windings 82 received within a recess 84 provided in sensor section 50 of the scan assembly 10, and secondary windings 86 received within a recess 88 in rear section 16 of the scan assembly 10. The windings 82, 86 are oriented so as to be substantially parallel to one another and are positioned so that a small air gap 90 exists therebetween. As can be appreciated by one skilled in the art, the more narrow air gap 90, the more efficient transformer 80. Since a voltage transformation is not desired or necessary, the turns ratio between primary windings 82 and secondary windings 86 is about 1:1. Further, since sensor section 50 is rotatable with respect to both front section 14 and rear section 16 of scan assembly 10, primary windings 82 of rotary transformer 80 are similarly rotatable with respect to secondary windings 86 thereof. In order to pass power and/or data through scan assembly 10, an additional transformer (not shown), substantially identical to transformer 80, may be incorporated at the rotating interface between sensor section 50 and front section 14.

Figure 8A:
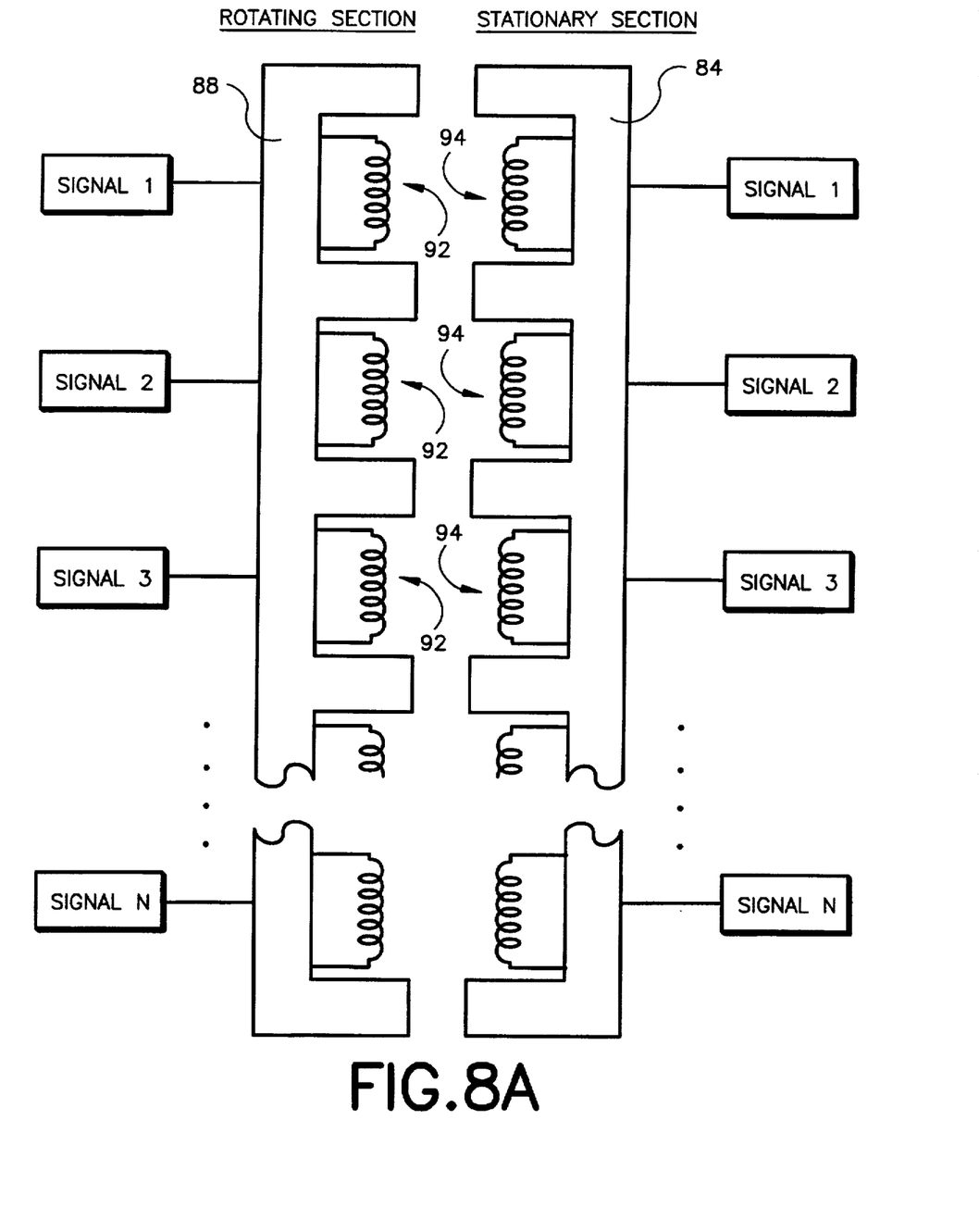
FIGS. 8A and 8B are schematic diagrams of two embodiments of a rotary transformer in accordance with the present invention.

The primary windings 82 comprises a plurality of individual windings 92 which are wound in a circular pattern, concentric with the central axis of scan assembly 10. Each individual winding 92 is dedicated to the transfer of a particular signal which is magnetically coupled to a corresponding individual winding 94 of secondary windings 86. For example, one pair of winding 92, 94 may be dedicated to the transfer of the signal controlling the pulse width of the interrogating pulse transmitted by the transducer 46. As another example, a pair of windings 92, 94 may be dedicated to the transfer of AC power to sensor section 50. Other signals that can be transferred across transformer 80 include but are not limited to gain controls for the transducer, video signals, and angular orientation controls for the transducer. Thus, the number pairs of individual windings 92,94 of transformer 80 is directly related to the number of signals which are to be transmitted across transformer 80. This is schematically illustrated in FIG. 8A where each signal 1,2,3, . . . N is associated with a pair of individual windings 92,94 for transmission across the rotating interface of scan assembly 10.

Figure 8B:
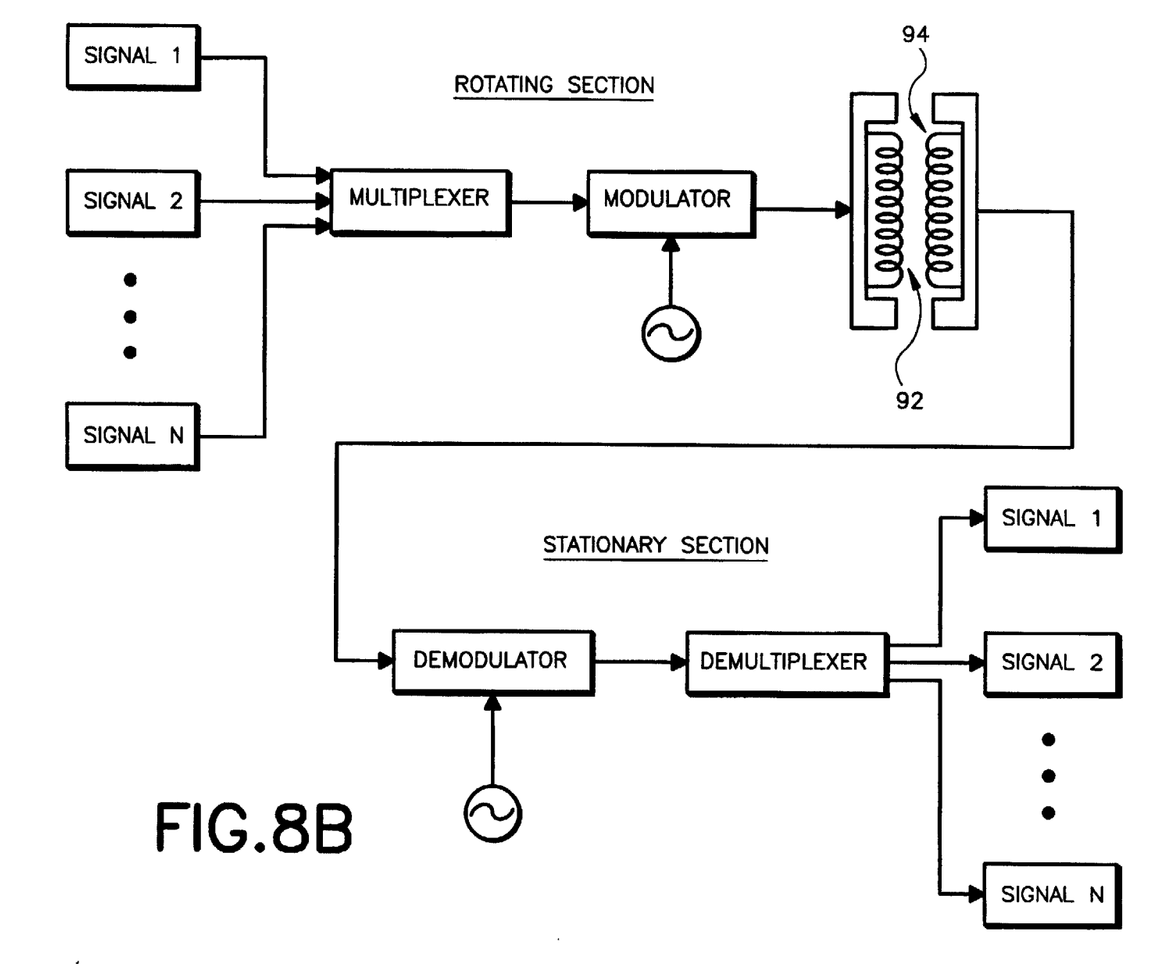

An alternative to having multiple pairs of dedicated windings another embodiment of transformer 80 comprises a single pair of windings 92, 94 wherein signals 1, 2, . . . N are multiplexed and then modulated onto a high frequency carrier signal, as illustrated in FIG. 8B. The modulated signal is magnetically coupled from the primary winding 92 to the secondary winding 94, and is then demodulated and demultiplexed back into separate signals 1,2,3, . . . N. For purposes of the present invention, any one of the numerous multiplex/modulation schemes known by those skilled in the art that is within the maximum frequency limits of the inductive reactance of the transformer 80 is suitable. In comparison, this approach takes less space but requires more support circuitry to multiplex and modulate the signals being transmitted.

In order to prevent cross-talk between the pairs of windings 92, 94, electrical shielding should be provided in recesses 84, 88 between adjacent windings 92,94 respectively, as shown in FIGS. 7 and 8A. It has been determined the use of a round aluminum plate (not shown) with concentric grooves therein for receiving individual windings 92 or 94 is suitable for such purposes, though one skilled in the art could use a variety of other insulating materials with satisfactory results. The individual windings 92 and 94 are placed in the concentric grooves of the respective aluminum plates for the primary and secondary windings. In place within transformer 80, the concentric grooves of corresponding windings 92, 94 face each other and align so that the windings are only separated by an air gap 90. Further, the smaller air gap 90 the more efficient the operation of transformer 80.

Figure 9:
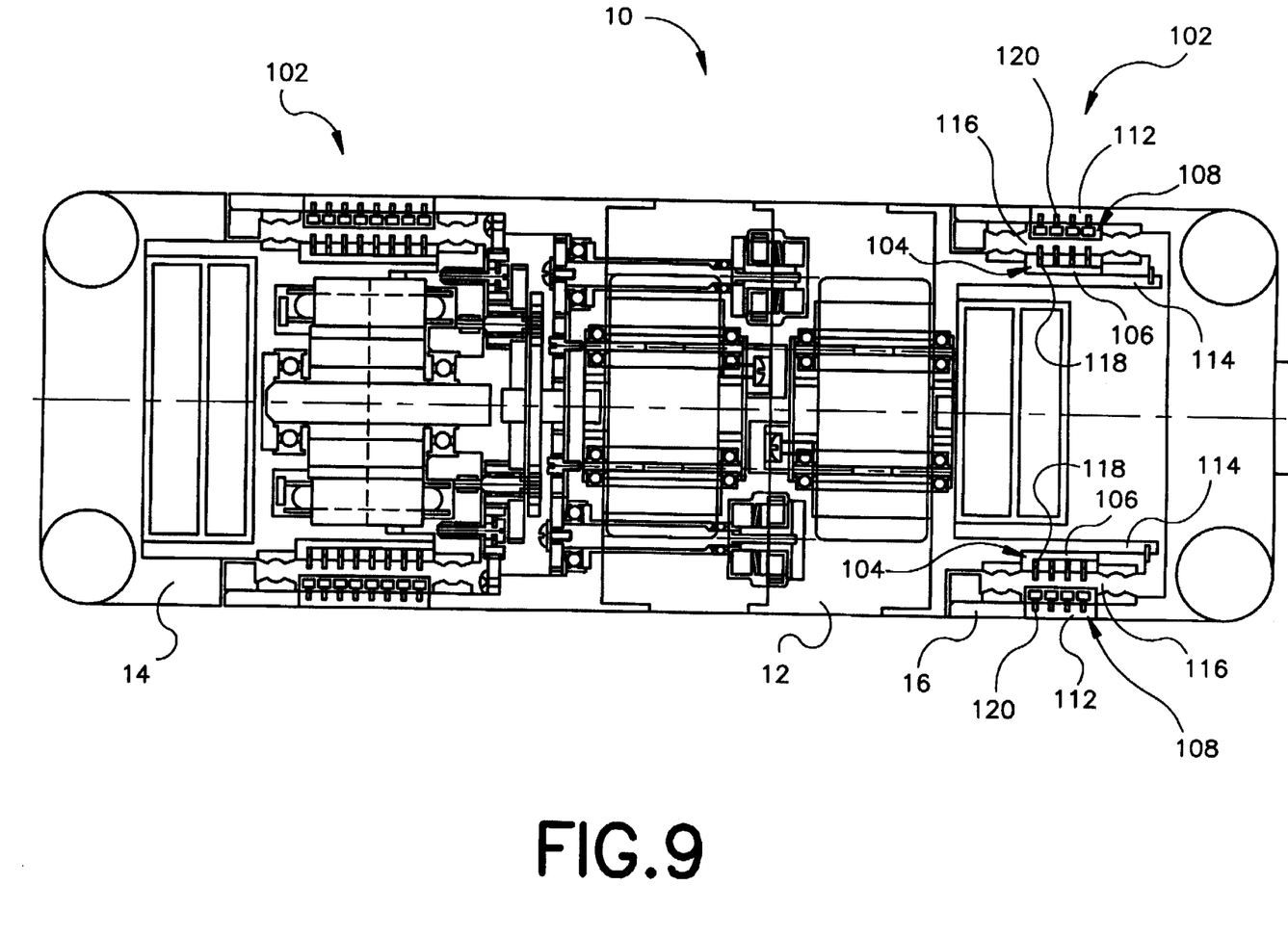
FIG. 9 is a cross-sectional view of a scan assembly showing a second embodiment of a rotary transformer in accordance with the present invention.

An alternate embodiment of a rotary transformer in accordance with the present invention is transformer 102, illustrated in FIG. 9 within the scan assembly 10 of FIG. 1, though it can be appreciated that transformer 102 can just as easily be incorporated within the scan assembly 10 of FIG. 4. In the presented configuration, rotary transformer 102 is comprised of primary windings 104 received within a recess 106 in a cylindrical flange 114 attached to sensor section 12 of scan assembly 10 and secondary windings 108 received within a recess 112 located in rear section 12.

In contrast to the previous embodiment of rotary transformer 80, the windings 104, 108 are concentric rather than parallel to each other, and the primary windings 104 being positioned within the secondary windings 108 so as to create an air gap 116 therebetween. The primary windings 104 include a plurality of individual windings 118, each of which correspond to an individual winding 120 of secondary windings 108. As with the previous embodiment, the pairs of individual windings 118, 120 may be dedicated to the transfer of a particular signal (see FIG. 8A) or transformer 102 can comprise a single pair of windings 118, 120 over which the signals are multiplexed and modulated and then demodulated and demultiplexed (see FIG. 8B).

Further, as with transformer 80, sensor section 12 is rotatable with respect to both front section 14 and rear section 16 of the scan assembly 10 and thus, the primary windings 104 of rotary transformer 102 are rotatable with respect to the secondary winding 108. Since the windings 104, 108 are concentric, rather than parallel, a more compact rotary transformer assembly results. A second transformer 102 is shown at the interface between front end section 14 and sensor section 12. This second transformer 102 allows control information, signal data and/or power to be transmitted in either direction through scan assembly 10 to another scan assembly located to the front or downstream of scan assembly 10.

Figure 10:
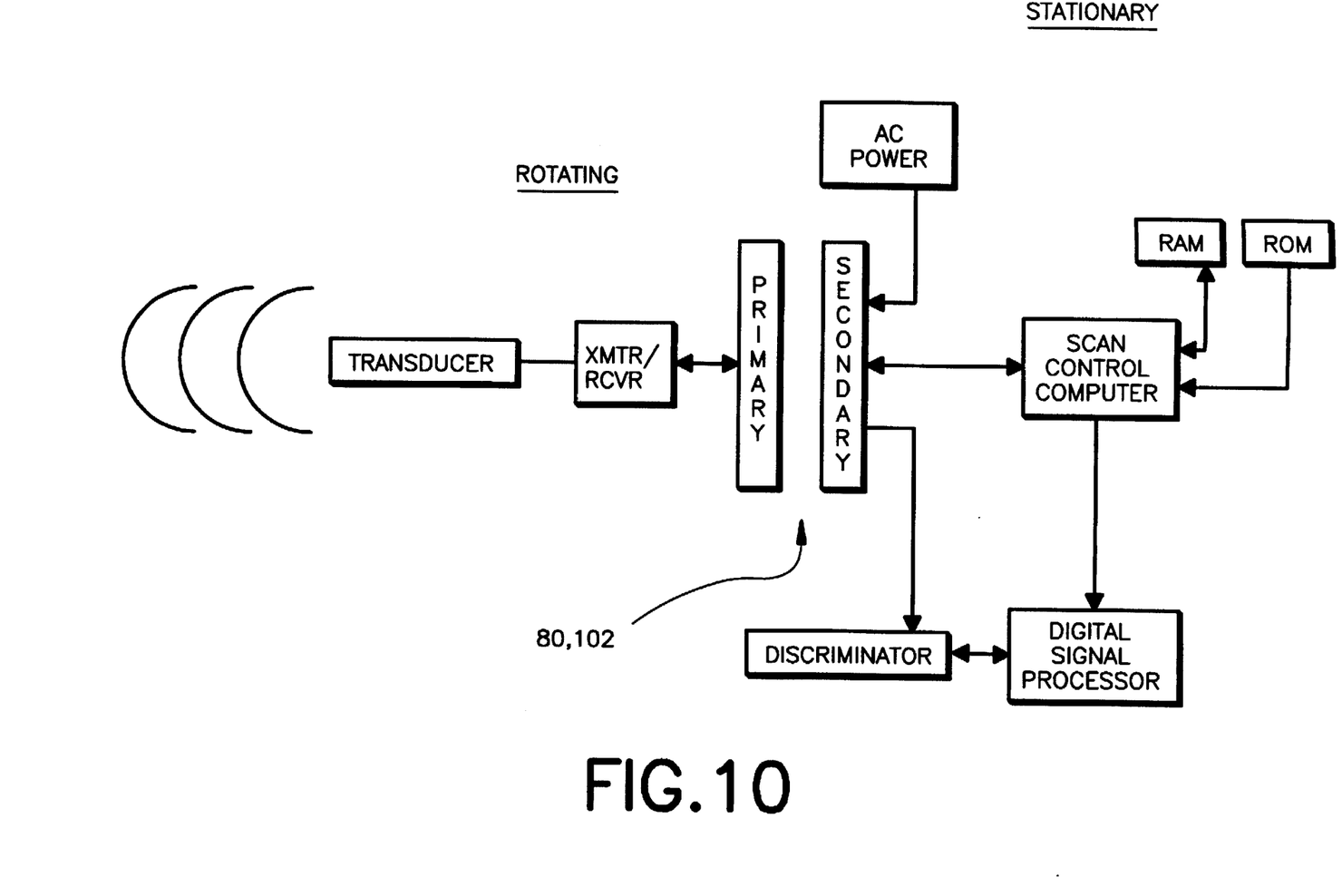
FIG. 10 is a schematic diagram of the sensor circuitry of a scan assembly with a rotary transformer in accordance with the present invention.

FIG. 10 is provided to illustrate the relationship of the rotary transformer 80, 102 with respect to the various other signal transmitting and processing components of the scan assembly 10. Worth noting is that control information, signal data and power can be transmitted in either direction across the rotary transformer 80, 102 as required for the operation of the transducer and/or the operation of scan assemblies in an inspection train of multiple scan assemblies and located downstream of scan assembly 10. For example, control information transmitted from the stationary end section 14, 16 to the rotating sensor section 16 for control of the interrogating pulse can include pulse width information, angular orientation information, power information, and receiver gain information.

Moreover, it will be understood that the invention is not restricted to the particular embodiments described herein, and that many modifications can be made to such embodiments by one skilled in the art without departing from the spirit of the invention as defined by the following claims.

Wherefore, the following is claimed:

1. A method for transferring power and a data signal across a rotating interface of a scan assembly used for inspecting gas pipes, said scan assembly comprising a rotating sensor section having a first electrical circuit and a stationary end section having a second electrical circuit, said first electrical circuit and said second electrical circuit forming a pair of corresponding electrical circuits, the rotating interface being defined by said sensor section and said stationary end section, and wherein a plurality of data signals are to be transmitted across the rotating interface, the method comprising the steps of:

multiplexing the plurality of data signals;

modulating said multiplexed signals onto a carrier signal;

placing said carrier signal on said first electrical circuit of said rotating sensor section;

magnetically coupling said first electrical circuit with said second electrical circuit;

decoupling said carrier signal at said second electrical circuit;

demodulating said data signals from said carrier signal; and demultiplexing said multiplexed data signals.

2. The method of claim 1, wherein first electrical circuit comprises circular windings and said second electrical circuit comprises circular windings, and wherein said windings of said first electrical circuit are parallel to said windings of said second electrical circuit.

3. The method of claim 1, wherein said first electrical circuit comprises circular windings and said second electrical circuit comprises circular windings, and wherein said windings of said first electrical circuit are concentric to said windings of said second electrical circuit.

4. A method for transferring power and a data signal across a rotating interface of a scan assembly used for inspecting gas pipes, said scan assembly comprising a rotating sensor section having a first electrical circuit and a stationary end section having a second electrical circuit, said first electrical circuit and said second electrical circuit forming a pair of corresponding electrical circuits, the rotating interface being defined by said sensor section and said stationary end section, the method comprising the steps of:

placing a carrier signal on said first electrical circuit of said rotating sensor section, said carrier signal having said data signal coupled thereto;

magnetically coupling said first electrical circuit with said second electrical circuit;

transferring said carrier signal from said first electrical circuit to said second electrical circuit; and decoupling said data signal from said carrier signal at said second electrical circuit;

wherein a plurality of data signals are transmitted across said rotating interface and wherein for each of said data signals there is a first electrical circuit on said sensor section and a corresponding second electrical circuit on said stationary end section.

5. The method of claim 4, wherein alternating current power is transmitted across said rotating interface by a rotary transformer, said rotary transformer including a first electrical circuit on said sensor section and a corresponding second electrical circuit on said stationary end section for the transfer of said alternating current power.

6. An ultrasonic scan assembly for use in inspecting downhole gas pipes comprising a rotary transformer defined by a sensor section which rotates in relation to an end section which remains essentially stationary, the sensor section including at least one ultrasonic transducer for transmitting interrogating pulses into a pipe wall and for receiving return pulses which are analyzed for maintenance and repair purposes, wherein the improvement comprises means for magnetically coupling return pulse data from said rotating sensor section to said stationary end section, and wherein a plurality of signals are transferred across said rotary transformer and for each of said signals there is a first winding on said sensor section and a corresponding second winding on said stationary end section.

7. The scan assembly of claim 6, wherein said magnetic coupling means comprises a rotary transformer including a first winding on said sensor section and a corresponding second winding on said stationary end section.

8. An ultrasonic scan assembly for use in inspecting downhole gas pipes comprising a rotary transformer defined by a sensor section which rotates in relation to an end section which remains essentially stationary, the sensor section including at least one ultrasonic transducer for transmitting interrogating pulses into a pipe wall and for receiving return pulses which are analyzed for maintenance and repair purposes, wherein the improvement comprises means for magnetically coupling return pulse data from said rotating sensor section to said stationary end section, and wherein a plurality of signals are transferred across said rotary transformer, and further comprising:

means for multiplexing said signals, said means located on said rotating sensor section;

means for modulating said multiplexed signals onto a carrier signal, said means located on said rotating sensor section;

means for demodulating said modulated signal, said means located on said stationary end section; and means for demultiplexing said multiplexed signals, said means located on said stationary end section.

\* \* \* \* \*